(12) United States Patent
Romero et al.

(10) Patent No.: US 10,894,030 B2
(45) Date of Patent: *Jan. 19, 2021

(54) METHODS AND COMPOSITIONS FOR THE INHIBITION OF THE EXPRESSION OF PD-L1 IN TUMOR CELLS

(71) Applicant: IN Ingredients, Inc., Columbia, TN (US)

(72) Inventors: Augustin T. Romero, Columbia, TN (US); Bolin Qin, Gaithersburg, MD (US)

(73) Assignee: IN Ingredients, Inc., Spring Hill, TN (US)

( * ) Notice: Subject to any disclaimer, the term of this patent is extended or adjusted under 35 U.S.C. 154(b) by 104 days.

This patent is subject to a terminal disclaimer.

(21) Appl. No.: 15/703,165

(22) Filed: Sep. 13, 2017

(65) Prior Publication Data

US 2019/0076393 A1    Mar. 14, 2019

(51) Int. Cl.
    *A61K 31/353*    (2006.01)

(52) U.S. Cl.
    CPC .................................. *A61K 31/353* (2013.01)

(58) Field of Classification Search
    CPC .................................................. A61K 31/353
    See application file for complete search history.

(56) References Cited

U.S. PATENT DOCUMENTS

| 10,478,418 B2 * | 11/2019 | Romero | A61K 36/53 |
| 2016/0324801 A1 | 11/2016 | Dixon et al. | |
| 2017/0151269 A1 | 6/2017 | von Maltzahn et al. | |

FOREIGN PATENT DOCUMENTS

| WO | 2011090666 A2 | 7/2011 | |
| WO | WO-2019055513 A1 * | 3/2019 | A61K 36/54 |

OTHER PUBLICATIONS

Yongli et al., "Function of PD-L1 in antitumor immunity of glioma cells", Saudi J. Biol. Sci., 2017, vol. 24, pp. 803-807; available online Jul. 2015 http://dx.doi.org/10.1016/j.sjbs.2015.06.025 (Year: 2015).*
Nduom et al., "PD-L1 expression and prognostic impact in glioblastoma", Neuro-Oncology, 2016, vol. 18, No. 2, pp. 195-205; available online Aug. 2015 https://doi.org/10.1093/neuonc/nov172 (Year: 2015).*
Xue et al., "Blocking the PD-1/PD-L1 pathway in glioma: a potential new treatment strategy", J. Hematol. Oncol., 2017, vol. 10, article 81 https://doi.org/10.1186/s13045-017-0455-6 (Year: 2017).*
Qin et al., "Cinnamon polyphenols regulate S100b, sirtuins, and neuroactive proteins in rat C6 glioma cells", Nutrition, 2014, vol. 30, pp. 210-217 (Year: 2014).*
Xue et al., "The prognostic significance of PD-L1 expression in patients with glioma: A meta-analysis", Scientific Reports, 2017, vol. 7, article 4231 | DOI:10.1038/s41598-017-04023-x available online Jun. 26, 2017 (Year: 2017).*
Mamelak et al. Expert Opinion on Drug Delivery, 2007, 4:2, 175-186 (Year: 2007).*
Connell et al., PLoS One, 2016; vol. 11; No. 10; e0165386, pp. 1-18; abstract; p. 14, fourth paragraph. DOI: 10.1371/journal.pone.0165386.
Watson et al., Elsevier, 2014; pp. 1-1426; p. 430, col. 1, paragraph 1.
Connell, Bridgette Janine et al, "A Cinnamon-Derived Procyanidin Compound Displays Anti-HIV-1 Activity by Blocking Heparan Sulfate- and Co-Receptor-Binding Sites on gp120 and Reverses T Cell Exhaustion via Impeding Tim-3 and PD-1 Upregulation," PLOS One 11(10): e0165386, DOI: 10.1371/journal.pone.0165386, Oct. 16, 2016.
Anderson, Richard A. et al, "Isolation and Characterization of Polyphenol Type-A Polymers from Cinnamon with Insulin-Like Biological Activity," J. Agric. Food Chem. 2004, 52, 65-70.
Chen, L. et al., Immunosuppressive Effects of A-Type Procyanidin Oligomers from Cinnamomum tamala, Evidence-Based Complementary and Alternative Medicine, vol. 2014, Article ID 365258, 9 pages; Year 2014.

* cited by examiner

*Primary Examiner* — James D. Anderson
(74) *Attorney, Agent, or Firm* — Dinsmore & Shohl LLP; Weston R. Gould

(57) ABSTRACT

Processes for decreasing expression of a CD274 gene and/or a PD-L1 protein in a subject in need of such expression changes are provided. The processes include administering to the subject a composition including at least 0.5% of an active ingredient by weight. The active ingredient includes cinnamtannin D1 and/or cinnamtannin B1. The processes further include decreasing expression of a CD274 gene and/or a PD-L1 protein in the subject by the step of administering.

16 Claims, 5 Drawing Sheets

US 10,894,030 B2

METHODS AND COMPOSITIONS FOR THE INHIBITION OF THE EXPRESSION OF PD-L1 IN TUMOR CELLS

FIELD

The present disclosure relates to the use of cinnamtannin B1 (CTB-1) and cinnamtannin D1 (CTD-1), methods for promoting decreased expression of a CD274 gene or a PD-L1 protein in a cell, including a tumor cell, and methods of treating a subject with cancer, including a subject with glioblastoma multiforme (GBM).

BACKGROUND

Dysregulated cellular function underlies many pathological conditions. Identification of molecular effectors of proper cell function along with methods of preventing or reversing cell dysfunction are required for promoting or maintaining proper or enhanced cellular function. Dysregulated gene expression is implicated in a variety of diseases such as cancer, diabetes, obesity, cardiovascular diseases and neurodegeneration. Discerning which molecular targets are most directly associated with a disease or condition is paramount to treating or preventing the disease and condition.

The programmed death 1 (PD-1) receptor and PD-1 ligands 1 and 2 (PD-L1, PD-L2) play integral roles in immune regulation. PD-1 is expressed on activated T-cells and activated by PD-L1 and PD-L2 expressed by stromal cells, tumor cells, or both. Activation of the PD-1 signaling initiates T-cell death and localized immune suppression potentially providing an immune-tolerant environment for tumor development and growth. Conversely, inhibition of this interaction can enhance local T-cell responses and mediate antitumor activity in nonclinical animal models. In the clinical setting, treatment with antibodies that block the PD-1-PD-L1 interaction have been reported to produce objective response rates of 7% to 38% in patients with advanced or metastatic solid tumors, with tolerable safety profiles.

Programmed death-ligand 1, PD-L1, (also called B7-H1 or CD274) is a 290 amino acid protein receptor ligand encoded by the CD274 gene and is expressed widely on both lymphoid and non-lymphoid tissues such as CD4 and CD8 T-cells, macrophage lineage cells, peripheral tissues as well as on tumor cells, and virally-infected cells (Dong, et al., *Nature Med.*, 1999; 5: 1365-1369). PD-L1 binds to receptors PD-1 and B7-1 which belong to the CD28/CTLA-4 (cytotoxic T lymphocyte antigen)/ICOS (inducible co-stimulator) family of T-cell co-inhibitory receptors and attenuates the immune response by inhibiting T-cell activation. PD-L1 binding to PD-1 or B7-1 results in decreased T-cell proliferation and cytokine secretion, compromising humoral and cellular immune responses in diseases such as cancer, and viral infection.

The expression of PD-L1 on tumor cells and virally-infected cells is exploited by tumors and chronic viral infections to evade immune response. PD-L1 is expressed on a wide variety of tumors and studies on animal models have shown that PD-L1 on tumors inhibits T-cell activation and lysis of tumor cells and may lead to increased death of tumor-specific T-cells. In chronic viral infections, PD-L1 expressed on virally-infected cells binds to PD-1 on virus-specific T-cells and these T-cells become "exhausted" with loss of effector functions and proliferative capacity. The PD-1-PD-L1 system also plays an important role in induced T-regulatory cell development and in sustaining T-regulatory cell function. Accordingly, as PD-L1 plays an important role in tumor immunity and infectious immunity, a composition that decreases expression of a CD274 gene or a PD-L1 protein is an ideal candidate for immunotherapy.

As such, there exists a need for compositions and methods of decreasing expression of a CD274 gene or a PD-L1 protein in a cell, including a tumor cell. Further, there exists a need for compositions and methods of treating a subject with cancer by decreasing expression of a CD274 gene or a PD-L1 protein in a cell, including a tumor cell.

SUMMARY

It is understood that both the following summary and the detailed description are exemplary and explanatory and are intended to provide further explanation of the disclosure as claimed. Neither the summary nor the description that follows is intended to define or limit the scope of the disclosure to the particular features mentioned in the summary or description.

One object is to provide a method for decreasing levels of a CD274 gene product(s) or a PD-L1 protein in a cell, optionally a tumor cell. This object is achieved in the present disclosure that provides processes for decreasing expression of a CD274 gene or a PD-L1 protein in a cell. In various embodiments, the processes include contacting a cell with an effective amount of cinnamtannin D1 and/or cinnamtannin B1. The cell may be, for example, a tumor cell. In certain embodiments, the tumor cell is a glial tumor cell, including a glioblastoma multiforme tumor cell. In further embodiments, the processes include administering to a subject a composition comprising at least 0.5% cinnamtannin D1 and/or cinnamtannin B1 by weight. Further processes include methods of treating a subject with cancer, including a subject with a glial tumor, including glioblastoma multiforme (GBM), by the step of administering to the subject a composition comprising at least 0.5% cinnamtannin D1 and/or cinnamtannin B1 by weight.

BRIEF DESCRIPTION OF THE DRAWINGS

Referring now to the illustrative examples in the drawings.

DETAILED DESCRIPTION

Figure 1:
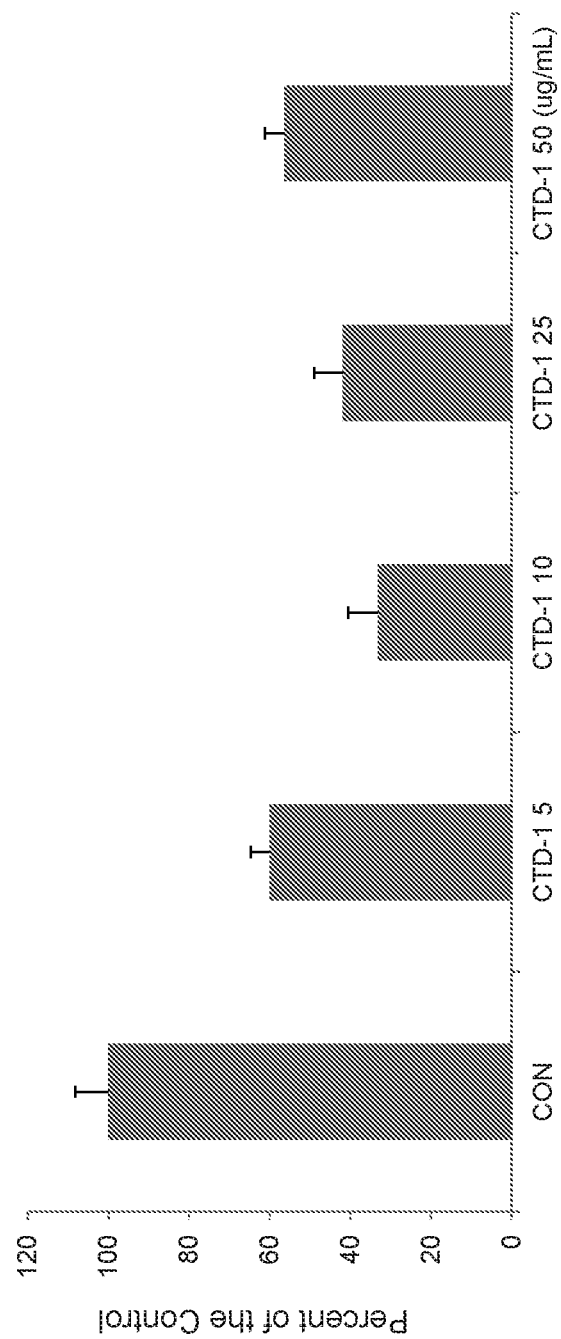
FIG. 1 graphically depicts the effects on PD-L1 expression as quantitative densitometry results of immunofluorescence studies for rat C6 glioma cells treated with cinnamtannin D1 at a concentration of at 0 µg/ml, 5 µg/ml, 10 µg/ml, 25 µg/ml, or 50 µg/ml for 24 hours at 37° C. where results are expressed as the mean±SD of five to ten random fields with approximately similar density of cells in each field in each plate.

The following description of particular embodiment(s) is merely exemplary in nature and is in no way intended to limit the scope of the invention, its application, or uses, which may, of course, vary. The disclosure is described with relation to the non-limiting definitions and terminology included herein. These definitions and terminology are not designed to function as a limitation on the scope or practice of the disclosure but are presented for illustrative and descriptive purposes only.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Various embodiments generally provide a composition that decreases expression of a CD274 gene or a PD-L1 protein in a cell. More particularly, the compositions and processes of various embodiments decrease expression of a CD274 gene or a PD-L1 protein in a cell and may be used for restoring normal expression of such chemicals, proteins, and expression products that may be due to dysfunctions of the PD-1/PD-L1 system or other cause. In various embodiments, the composition includes cinnamtannin D1 and/or cinnamtannin B1. Further, the various embodiments include methods of treating a subject with cancer, including a subject with a glial tumor, including glioblastoma multiforme (GBM), by the step of administering to the subject a composition comprising at least 0.5% cinnamtannin D1 and/or cinnamtannin B1 by weight.

Processes are provided for decreasing or even inhibiting expression of a CD274 gene and/or a PD-L1 protein in a cell. In some embodiments, processes for decreasing expression of a CD274 gene or a PD-L1 protein in a cell include contacting a cell with an effective amount of cinnamtannin D1 and/or cinnamtannin B1. The cell may be, for example, a cell that has increased cellular levels of a CD274 gene and/or a PD-L1 protein relative to normal cellular levels. In various embodiments, the cell is a tumor cell, such as, by way of example and not limitation, a glial tumor cell, such as a glioblastoma multiforme cell. In various embodiments, processes are provided for altering expression of a CD274 gene and/or a PD-L1 protein in a cell of a subject.

As used herein, a "subject" is defined as an organism (such as a human, non-human primate, equine, bovine, murine, or other mammal). In some embodiments a subject is a cell. A cell may include a tumor cell, such as a glial tumor cell, including but not limited to a glioblastoma multiforme cell. As used herein, "a subject in need" is defined as a subject that has undesirable cellular expression levels of a CD274 gene and/or a PD-L1 protein, optionally higher expression of a CD274 gene and/or a PD-L1 protein relative to normal cellular levels, or that desires to have decreased cellular levels of a CD274 gene and/or a PD-L1 protein relative to normal cellular levels or the subject's own cellular baseline levels.

The term "inhibiting" is defined as a decrease in expression, activity, or effect relative to a control related to the presence of an effector, such as an active ingredient (as provided herein) or a component thereof. Illustrative examples of "inhibiting" are decreases in the cellular expression level or rate of one or more genes that encode PD-L1 such as CD274, or decreases in levels of a PD-L1 protein.

"Active ingredient" refers a component present in the composition that renders, directly or indirectly, the intended effect. Particular examples are cinnamtannin D1 and/or cinnamtannin B1. In some embodiments other polyphenol type-A polymers may be used, with more particular examples being singly linked type-A polymers and/or doubly linked type-A polymers. In some embodiments, the term "active ingredient" excludes singly linked Type-A polymers.

"Polyphenol" as used herein refers to a group of chemical substances found in plants, characterized by the presence of more than one phenol group per molecule. For purposes of this disclosure, it is to be understood that polyphenols include, but are not limited to, Type-A polymers and oligomers or phenolic materials. Natural sources of polyphenols include green tea, white tea, red wine, dark chocolate, olive oil, and other fruits, vegetables, and plants including cinnamon.

In various embodiments, the composition includes at least 0.5% Type-A polymers by dry weight. Type-A polymers may include A-Type singly and/or doubly linked procyanidin oligomers of the catechins and/or epicatechins. Such A-Type singly linked procyanidin oligomers of the catechins and/or epicatechins can include A-Type singly linked procyanidin dimers, A-Type singly linked procyanidin trimers, A-Type singly linked procyanidin trimers, A-Type singly linked procyanidin tetramers, and/or a mixture of A-Type singly linked procyanidin oligomers. Such A-Type doubly linked procyanidin oligomers of the catechins and/or epicatechins can include A-Type doubly linked procyanidin dimers, A-Type doubly linked procyanidin trimers, A-Type doubly linked procyanidin trimers, A-Type doubly linked procyanidin tetramers, and/or a mixture of A-Type doubly linked procyanidin oligomers. In various embodiments, the A-Type doubly linked procyanidin oligomers of the catechins and/or epicatechins include cinnamtannin D1 and/or cinnamtannin B1.

Type-A polymers as used herein are a bioactive type of naturally available polymers. They are identified by their protonated molecular masses as A-type singly or doubly linked procyanidin oligomers of the catechins and/or epicatechins. The polymers are composed of monomeric units of catechins and/or epicatechins with a molecular mass of 288 Da. A-type doubly linked procyanidin oligomers may have masses ranging from 576 to 1728 Da and may include dimers, trimers, tetramers, and a mixture of oligomers, respectively. For example, two separate doubly linked Type A trimers and a doubly linked Type A tetramer have molecular masses of 864 and 1152 Da, respectively. The trimer and tetramer oligomers include terminal (T), middle (M) and base (B) units, with the M unit of the two trimers consisting of a single catechin/epicatechin and the M unit of the tetramer consisting of two catechins/epicatechins. Doubly linked procyanidin type-A oligomers of the catechins and/or epicatechins contain C4→C8 carbon and C2→O7 ether bonds between the T and M units of the oligomers, and have the structure:

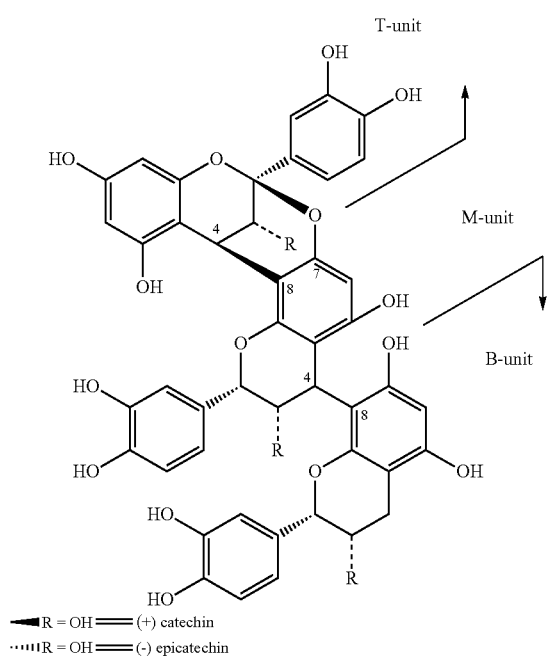

(Anderson et al., *J. Agric. Food Chem.*, 2004; 52:65-70.) Thus, in certain embodiments, Type-A polymers can include A-type singly or doubly linked procyanidin dimers of catechins and/or epicatechins, A-type singly or doubly linked procyanidin trimers of catechins and/or epicatechins, A-Type singly or doubly linked procyanidin tetramers of catechins and/or epicatechins, and/or a mixture of A-Type singly or doubly linked procyanidin oligomers of catechins and/or epicatechins. In other embodiments, Type-A polymers can include A-Type doubly linked procyanidin dimers of catechins and/or epicatechins, A-type doubly linked procyanidin trimers of catechins and/or epicatechins, A-Type doubly linked procyanidin tetramers of catechins and/or epicatechins, and/or a mixture of A-Type doubly linked procyanidin oligomers of catechins and/or epicatechins. In some embodiments, A-Type singly linked procyanidin oligomers of the catechins and/or epicatechins are excluded from a composition.

In some embodiments, the Type-A polymers can include cinnamtannin D1 ((2R,3R,4S,8S,14R,15R)-2,8-bis(3,4-dihydroxyphenyl)-4-[(2R,3S)-2-(3,4-dihydroxyphenyl)-3,5,7-trihydroxy-3,4-dihydro-2H-1-benzopyran-8-yl]-3,4-dihydro-2H,8H,14H-8,14-methano-1,7,9-trioxabenzo[6,7]cycloocta[1,2-a]naphthalene-3,5,11,13,15-pentol) and/or cinnamtannin B1. Cinnamtannin D1 has the following structure:

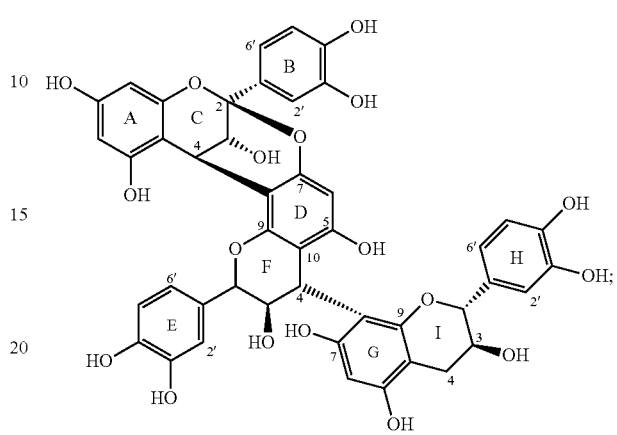

and
Cinnamtannin B1 has the following structure:

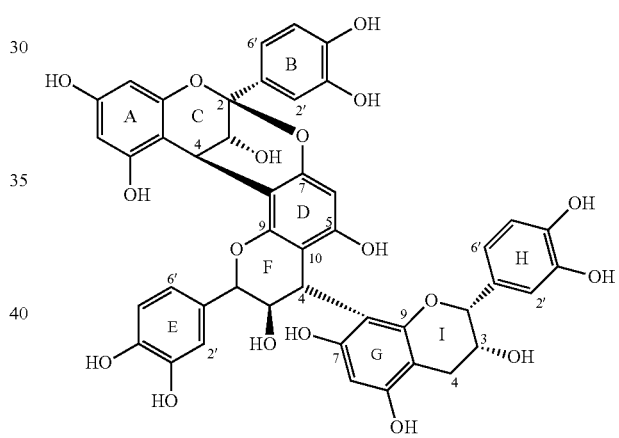

In some embodiments, the amount of active ingredient (e.g., cinnamtannin D1 or cinnamtannin B1) is in the range of 0.5% to 25%, optionally 1% to 10% by weight. For example, the amount of active ingredient is greater than or equal to 0.5%, greater than or equal to 1%, greater than or equal to 2%, greater than or equal to 3%, greater than or equal to 4%, greater than or equal to 5%, greater than or equal to 10% by weight. In some embodiments, an active ingredient is or is a part of a broader composition. For example, the active ingredient may be present in the broader composition at 0.5%-100% by weight, 1%-50% by weight, 1%-10% by weight, 20%-50% by weight, 30%-40% by weight, or any value or range between 0.5% and 100% of the dry weight of the broader composition.

Type-A polymers such as A-Type singly and/or doubly linked procyanidin oligomers of the catechins and/or epicatechins such as cinnamtannin D1 or cinnamtannin B1 may be chemically synthesized or obtained from one or more natural sources. One or more of any process for isolating chemical material from a plant may be used to isolate the Type-A polymers such as A-Type singly and/or doubly linked procyanidin oligomers of the catechins and/or epicatechins. One exemplary source of type-A polymers is cinnamon. Cinnamon may be obtained from various resources. Illustratively, cinnamon is obtained from bark. Cinnamon bark may be obtained from various parts of the world, including China, Sri Lanka, Indonesia and others. The type-A polymers are optionally obtained by carefully tailored extraction procedures from cinnamon bark. An extract of cinnamon is optionally derived from any Cinnamonum species. In an exemplary embodiment, an extract of cinnamon is derived from the bark of Cinnamonum aromaticum, Cinnamonum verum, or Cinnamomum burmannii. In some embodiments, an extract of cinnamon is derived from the bark of the Cinnamomum zeylanicum tree of the genus Lauraceae. This tree is native to eastern and southeastern Asia. Other sources of cinnamon may also be used in the methods and materials disclosed herein. Cinnamon bark may be used in the form of raw bark, sliced, or minced bark, or pulverized bark for the preparation of the therapeutic materials, and pulverized cinnamon bark is used in particular instances.

Extracts may be prepared by various methods carefully tailored to produce the required concentration or amount of type-A polymers. The extracts are optionally water soluble. As such, the extracts are optionally water soluble water extracts, water soluble alcohol extracts, or water soluble extracts of other operative extraction processes. The extraction process is directly linked to the final composition of the resulting extract. As such, a product formed by one process does not necessarily equate to an extract formed by a different process, often differing by a single extraction parameter. The processes described herein represent exemplary methods to produce extracts with the desired level of the active agent—Type-A polyphenols, particularly doubly linked Type-A polymers.

Extraction parameters such as water quality, heating temperature, drying temperature, heating time, drying time, and filtering processes all contribute to the quality and efficiency of the processes. Water quality directly affects the concentration of active agents. Poor quality water may cause type-A polymers to become decomposed and oxidized during the extraction process. This often results in cinnamon extract powder being reddish in color and the percent concentration of type-A polymers being low. Heating time determines the ratio of various polymers being extracted. Heating time also affects the thickness of extraction mixture which then has a direct impact on the downstream filtering process. The temperature of the extraction also affects the level of active type-A polymers. In some embodiments, the extraction temperature is between 50° C. and 100° C. Optionally, the extractions temperature is between 50° C. and 95° C. Optionally, the temperature is between 50° C. and 90° C. Optionally the extraction temperature is between 50° C. and 90° C. Drying temperature may vary from 75° C. to 120° C. depending on what other extraction parameters are also used. The amount of solvent used is generally from 2 to 100 times the raw extract material on a weight basis. Illustratively, when 50 g of cinnamon bark is used, the extraction is performed with 1000 ml of water (1 g/ml is weight of water—i.e. 20 times volume).

Extraction time is also important for obtaining the desired amount of, polyphenol Type-A polymers, which are described in detail above. Extractions are optionally performed by heating the raw material in an extraction solvent in excess of 10 minutes, optionally, in excess of 1 hour, optionally between 1 and 3 hours with any subdivision also operable.

Extraction solvents are optionally aqueous or organic. Distilled water or alcohols such as ethanol are optionally used alone or in combination as extraction solvents. The extracts obtained are optionally water soluble.

Achieving the necessary therapeutic effects of an extracted polyphenol composition requires steps beyond simple water or alcohol extraction. In some embodiments, liquid extracts are further processed by column chromatography to further isolate the actives, optionally by molecular sieve column appropriately sized to isolate the active.

Illustrative examples of cinnamon extracts that contain the requisite amount of type-A polymers are found in U.S. Pat. No. 6,200,569, which is hereby incorporated by reference in its entirety, and therein describing the product sold as CINNULIN PF. Optionally, doubly linked procyanidin type-A polymers (3% by weight) in a dried extract of bark from C. burmanni may be prepared as described (Anderson et al., J. Agric. Food Chem. 2004; 52:65-70), or provided by IN Ingredients Inc. (formerly Integrity Nutraceuticals, Columbia, Tenn., USA) as CINNULIN PF.

In some embodiments, 50 g clean cinnamon bark is ground into small particles or powder. The powder or particles are mixed with 1000 ml distilled water in a suitable flask. The mixture is let stand at room temperature for about 0.5 hour. In this and other examples, an amount of buffer is optionally added to maintain the pH of the extraction solvent. Additional water may be added is in the range of 1:20 to 1:2000. Too little water may render the mixture too thick for extraction. However, too much water increases drying time. Then the water mixture is heated while being stirred through the use of a magnetic heat stirrer. The temperature and extraction time are crucial to the concentration efficiency of the bioactive polymers. The extraction process is optionally no longer than one hour. Optionally, the ground bark may be heated for 15-20 minutes bringing to a boil, simmering for 20-30 minutes while stirring constantly. Optionally, the ground bark is heated to 100° C. 15-20 minutes and then simmered for 20-30 minutes while stirring constantly. The boiling time is optionally controlled at about 20-25 minutes following heating. The mixture is cooled and stored at 4° C. overnight. An exemplary cinnamon extract obtained by a water extraction is sold as CINNULIN PF.

In one embodiment, 250 kg of Cinnamomum burmannii, is ground into small particles or powder. The powder or particles are mixed with 2000 ml (8X) distilled ethanol-water in a suitable flask and the mixture is allowed to stand at ambient temperature for 0.5 hours. Optionally, water alone is used as the extraction solvent illustratively by using a 10X fold-water volume/weight ground cinnamon bark. The mixture is heated to 50° C. while being stirred through the use of a magnetic heat stirrer and circulated for 120 min. Evaporation is performed at a steam temperature of less than 100° C. with a process temperature of less than 60° C. with a TS refract meter of 45-50%. The liquid extract is filtered and further purified as above. The material is then dried to a moisture content of less than 5%.

In some embodiments, Type-A polyphenols are extracted from cinnamon using the following process: 5 g cinnamon and 100 ml 0.1 N acetic acid are combined and autoclaved for 15 minutes. The resultant mixture is cooled, then centrifuged and the precipitate discarded. Four volumes of ethanol/0.1 N acetic acid are added to the supernatant and the mixture is stored overnight at 4° C. The mixture is screened through a filter. To determine the amount of bioactive polymers the mixture is introduced onto an LH-20 column and washed with 600 ml ethanol/0.1 N acetic acid. The desired fraction is then eluted with a 1:1 mixture of acetonitrile and 0.2 N acetic acid. The eluate is then concentrated and introduced onto a HPLC column at 275 nm.

In some embodiments, the initial extraction is performed in the absence of acid. 50 g clean cinnamon bark is ground into small particles or powder and mixed with 1000 ml distilled water/10% ethanol in a suitable flask. Then the water mixture is heated while being stirred through the use of a magnetic heat stirrer. The extraction process is optionally no longer than one hour. Optionally, the ground bark in extraction solvent is heated to a boil for 15-20 minutes, and then simmered for 20-30 minutes while stirring constantly. The boiling time is typically controlled at about 20-25 minutes following heating. The mixture is cooled and stored at 4° C. overnight. It is appreciated that alcohols other than or in addition to ethanol, illustratively methanol, may be used in the extraction procedure as well. When alcohol is used in the extraction solvent is it generally present at 50% or less.

Any one of the extraction solutions (or combinations thereof) described herein is optionally filtered through a filter paper to remove any solid debris. If the solution is too thick for the filter paper, the removal of solids from the solution is optionally done with the use of centrifugation. The resulting supernatant is filtered through medium speed filter paper. The resulting solids are optionally dissolved in 200 mL distilled water, or water/ethanol for a second extraction. The liquid solution containing the solids is mixed and heated for 30 minutes at 80-90° C. and then is filtered to produce a second extraction solution.

In some embodiments, first and second extraction solutions are combined together and poured onto nonstick tray and allowed to dry at 80-90° C. Vacuum-spray dry equipment is optionally used for the drying procedure. The resulting dry extract powder is weighed. An extraction ratio is calculated as w/20×100% with was the weight (g) of the dry extract powder. The sample and water ratio, heat time, volume of water in the second extraction may vary depending on the amount of the raw material used for extraction.

High performance liquid chromatography (HPLC) is optionally employed to analyze the effect on the concentrations of the polymers by changes in heating temperature and extraction time. As a non-limiting example, 100 mg dry cinnamon powder is dissolved with 100 ml water in a flask. The solution is sonicated for 30-45 minutes and filtered through 0.45 μm PTFE syringe. The samples are prepared and tested at different temperatures as follows: samples are extracted at 50-60° C. for one hour, Type-A polymers eluting at 17 and 21 minutes have reasonable concentrations. After increasing the temperature to 75-82° C. for 1 hour, the peaks eluting at 17 and 21 minutes are decreased by 2-3%. There are additional two relatively small peaks that seem to surface during this extraction. They elute at 28.5 minutes, 33.5 minutes respectively. After the heating temperature is increased to 85-90° C. for an additional 1 hour, the peaks eluting at 17 and 21 minutes are decreased about 7-9%. The peaks at 28.5 and 33.5 increase significantly. Lastly, the heating temperature is increased to 95-100° C. for 20 minutes and then reduced to 85-95° C. for an additional 40 minutes. The peaks eluting at 17 and 21 minutes seem to decrease by 15-20%. The peaks eluting at 28.5 and 33.5 minutes increase by more than double. According to these results, the polymers at 17 and 21 minutes are converted to isomers at 28.5 and 33.5 minutes respectively.

In another procedure, the stabilization of the Type-A polymers is analyzed. Various extraction periods at heating temperature of 50-100° C. are tested particularly 95-100° C. After samples are extracted at 50-100° C. for one hour, polymer eluting at 17 and 21 minutes presents desirable concentrations. The peaks eluting at 17 and 21 minutes decrease as the heating temperature increases in the first 2-3 hours. After 3 hours, the peaks eluting at 17 and 21 minutes no longer change as significantly and seem to reach a plateau period. These results suggest that after a 3 hour extraction time at temperature of 95-100° C., polymers are stabilized.

Not only is it important to note that the time and temperature play a key factor in sustaining higher concentrations of these Type-A polymer key actives, additionally the species of choice can have a dramatic impact on the levels of these Type-A polymers. After thorough review of the world's many species of cinnamon, the following has proven to provide the highest level of active Type-A polymers: *Cinnamomum Burmannii* (Nees) Blume—Microbial Identification Index (MIDI) class; Korintji Cassia.

Cinnamon extract dry powder prepared as discussed above is tested to confirm the presence of certain amount of polyphenols such as double-linked polyphenol Type-A polymers (which may include A-Type doubly linked procyanidin dimers of catechins and/or epicatechins, A-Type doubly linked procyanidin trimers of catechins and/or epicatechins, A-Type doubly linked procyanidin tetramers of catechins and/or epicatechins, and/or a mixture of A-Type doubly linked procyanidin oligomers of catechins and/or epicatechins), singly-linked Type-A polymers (which may include A-Type singly linked procyanidin dimers of catechins and/or epicatechins, A-Type singly linked procyanidin trimers of catechins and/or epicatechins, A-Type singly linked procyanidin tetramers of catechins and/or epicatechins, and/or a mixture of A-Type singly linked procyanidin oligomers of catechins and/or epicatechins), or other bioactive polymers through the use of HPLC. In various embodiments, the Type-A polymers may include cinnamtannin D1 and/or cinnamtannin B 1. This allows for standardization of the extract.

In particular instances, the dry weight of the cinnamon extract powder can be standardized on the basis of a bioactive component, such as doubly-linked polyphenol Type-A polymers. As described above, doubly-linked polyphenol Type-A polymers may include A-Type doubly linked procyanidin dimers of catechins and/or epicatechins, A-Type doubly linked procyanidin trimers of catechins and/or epicatechins, A-Type doubly linked procyanidin tetramers of catechins and/or epicatechins, and/or a mixture of A-Type doubly linked procyanidin oligomers of catechins and/or epicatechins. In various embodiments, the A-Type doubly linked procyanidin oligomers of the catechins and/or epicatechins include cinnamtannin D1 and/or cinnamtannin B1. The amount of polyphenol Type-A polymers or the like is optionally in the range of 0.5% to 25%, optionally 1% to 10% by weight. Optionally, the amount of polyphenol Type-A polymers is greater than 0.5%, greater than 1%, greater than 2%, greater than 3%, greater than 4%, greater than 5%, or greater than 10% by weight. In further embodiments, the amount of doubly-linked polyphenol Type-A polymers or the like is optionally in the range of 0.5% to 25%, optionally 1% to 10% by weight. Optionally, the amount of doubly-linked polyphenol Type-A polymers is greater than 0.5%, greater than 1%, greater than 2%, greater than 3%, greater than 4%, greater than 5%, or greater than 10% by weight.

Depending on the source material, extraction procedures, extraction solvents, purification and concentration steps, etc., the final concentration of Type-A polymers is often insufficient or less than 0.5%, less than 1%, less than 2%, less than 3%, less than 4%, less than 5%, or less than 10% by weight. As such, the extract may be further processed to concentrate the type-A polymers to the desired or necessary concentration. A liquid extract is optionally passed over a column to provide a concentrated eluant with the target concentration of type-A polymers.

Cinnamon bark may be used in the form of raw bark, sliced, or minced bark, or pulverized bark for the preparation of the therapeutic materials, and pulverized cinnamon bark is used in particular instances.

In one experimental series, an extract is prepared according to the foregoing procedures using a water extraction solvent. The concentration of the sample is approximately (e.g., within error) 5.17 mg/ml. It is also very important to note that the concentrations of the polymers change with the temperature and extraction time.

Depending on the intended mode of administration, the composition administered can be in pharmaceutical compositions in the form of solid, semi-solid or liquid dosage forms, such as, for example, tablets, suppositories, pills, capsules, powders, liquids, oil based forms, or suspensions, and may be provided in unit dosages suitable for a single administration. Time release preparations are specifically contemplated as effective dosage formulations. The compositions will include an effective amount of the selected substrate in combination with a pharmaceutically acceptable carrier and, in addition, may include other medicinal agents, pharmaceutical agents, carriers, or diluents.

In embodiments in which the composition is a solid composition, conventional nontoxic solid carriers may include, for example, pharmaceutical grades of mannitol, lactose, starch, magnesium stearate, sodium saccharine, talc, cellulose, glucose, sucrose and magnesium carbonate. Liquid pharmaceutically administrable compositions may, for example, be prepared by dissolving or dispersing an active agent with optimal pharmaceutical adjuvants in an excipient, such as water, saline, aqueous dextrose, glycerol, or ethanol, to form a solution or suspension. For example, the pharmaceutical composition may contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's The Science and Practice of Pharmacy (20$^{th}$ Edition).

In various embodiments including oral administration, fine powders or granules may contain diluting, dispersing, or surface active agents. The fine powders or granules may be presented in water or in syrup, in capsules or sachets in the dry state, or in a non-aqueous solution or suspension. Suspending agents may also be included in tablets, which may include binders and lubricants in a suspension. Flavoring, preserving, suspending, thickening, or emulsifying agents may be also included to modify the taste and texture of the composition. The tablets and granules provided for oral administration may further be coated for ease of digestion.

In some embodiments, the composition containing the active Type-A polymers may be combined with one or more supplementary active agents. A supplementary active agent optionally functions synergistically with a Type-A polymer. Supplementary active agents illustratively include vitamins (such as vitamin A, vitamin B, vitamin C, vitamin D, vitamin E or vitamin K), antioxidants (such as acai, wolfberry, alpha lipoic acid, astazanthin, or fucoxanthin), or any combination of the above.

The composition including Type-A polymers may be in the form of a food additive. Examples include foods in a liquid, semi-liquid, solid, paste, or jelly form.

Compositions may be metabolized in the subject to yield a therapeutically effective amount of compound species, namely polyphenols such as a Type-A polyphenols as discussed in detail above, cinnamon oligomer, cinnamon catechin or epicatechin, cinnamon chalcone, and cinnamon MHCP. In particular therapies, each dose of the cinnamon extract supplement is selected so as to deliver into the individual Type-A polymers in the amount of 0.1 milligrams (mg) to 150 mg of Type-A polymer per serving or any value or range therebetween, optionally 1-30 mg, and optionally 3-10 mg.

In an exemplary regimen, the composition is taken orally between one and three times daily. However, it is contemplated that other routes of administration may be utilized. Also, it should be noted that the compositions may be utilized in the form of derivatives. For example, the composition may be bonded, chemically or physically, to other chemical species and moieties such as synthetic polymers, liposomes, small organic molecules, chitin, chitosan, other biopolymers and the like. In view of the teaching presented herein, still further combinations will be readily apparent to those of skill in the art.

In various embodiments, a subject is administered a composition in a dosage so that each dose of the compositions is selected to deliver into the Type-A polymers in the amount of 0.1 milligrams (mg) to 150 mg of Type-A Polymer per serving or any value or range therebetween, optionally 1-30 mg, optionally 3-10 mg. It is further contemplated that variable dosing regiments are operative in the processes. While in some instances, a single dose treatment may be effective in producing therapeutic or other desired effects, in other instances a treatment period in the range of, for example, six weeks to three or six months or more may be utilized.

The composition may be administered orally, parentally, or intravenously by intramuscular, intraperitoneally, by transdermal injection, or by contact with a cell or tissue such as by immersion or other form of contact. Injectable or oral dosage forms may be prepared in conventional forms, either liquid solutions or suspensions, solid forms suitable for solution or prior to administration, or as suspension in liquid prior to administration or as emulsions. Additionally, the dosage forms may be an oil-based form.

The dose of the composition may vary depending on the age, weight, general condition of the subject. For example, dosage in the range of 1-1,000 mg or equivalent of at least 0.5% Type-A polymers by dry weight per day may be an effective range. The active agent may be present at 0.01%-100% of the dry weight of the composition. For example, an active agent may comprise 0.5%-50% of the dry weight of the composition.

Administration of a composition to a subject (e.g., a cell) will inhibit expression of a PD-L1 gene or protein in a subject (e.g., in a cell) relative to control or baseline. Illustratively, a PD-L1 gene expression (such as CD274) is decreased as measured by the level of PD-L1 mRNA (such as CD274 mRNA) relative to a control such as the absence of composition. Illustratively, PD-L1 gene expression is inhibited (e.g., decreased) by a value of 1% to 300% or more relative to prior or control expression levels, or any value or range therebetween. Optionally, PD-L1 gene expression is decreased by 1%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or more relative to control or prior expression levels.

Methods for detecting mRNA expression to determine the presence or extent of gene expression are known in the art. Illustratively, mRNA is detected and optionally quantified by real-time polymerase chain reaction (qRT-PCR as used herein). qRT-PCR is optionally coupled to prior synthesis of cDNA from total cellular RNA such as using Superscript II RT which is a reverse transcriptase enzyme produced by Invitrogen, Corp., Carlsbad, Calif. Illustrative protocols for measuring gene expression can be found in Crujeiras A B, et al., *Eur J Clin Invest*, 2008; 38(9):672-8, as well as in other sources known in the art.

Detecting and optionally quantifying PD-L1 protein expression is achieved by many methods known in the art. Illustratively, PD-L1 protein expression is detected and optionally quantified by enzyme linked immunosorbent assay (ELISA), mass spectrometry, western blot, gel electrophoresis optionally coupled with staining such as by Coomassie brilliant blue or silver stain, or by target specific stains, flow cytometry, immunoprecipitation, or by other method known in the art. In some embodiments, an ELISA is used to detect and optionally quantify PD-L1 protein expression. For example, ELISA kits for PD-L1 are available from sources known in the art. Antibodies directed to PD-L1 proteins suitable for use in ELISA are available from sources known in the art, including Santa Cruz Biotechnology, Santa Cruz, Calif.

It is appreciated that any active ingredient described herein or their equivalents are optionally used in a process to treat dysfunctions of the PD-1/PD-L1 system in a subject (e.g., in a cell of a subject), including dysregulated PD-L1 levels and particularly high PD-L1 levels, as well as symptoms in a subject caused by such dysfunctions of the PD-1/PD-L1 system in a subject (e.g., in a cell of a subject).

A process of treating dysfunctions of the PD-1/PD-L1 pathway in a subject, including dysregulated PD-L1 levels and particularly high PD-L1 levels, is also provided. Such processes illustratively include administering to a subject a therapeutically effective amount of a composition including one or more Type-A polymers. A therapeutically effective amount is defined as that capable of decreasing the expression of a PD-L1 protein or a gene encoding a PD-L1 protein (such as CD274) in a subject (e.g., in a cell) relative to a control.

Processes of treating dysfunctions of the PD-1/PD-L1 pathway in a cell, including dysregulated PD-L1 levels and particularly high PD-L1 levels, illustratively include administering to a subject a dietary supplement composition including one or more active ingredients in a dosage so that each dose of the composition will deliver into the individual the active ingredient(s) in the amount of 0.1 milligrams (mg) to 150 mg per serving or any value or range therebetween, such as 1-30 mg, or 3-10 mg.

A process of treating symptoms implicated by dysfunctions of the PD-1/PD-L1 pathway (such as dysregulated PD-L1 levels and particularly high PD-L1 levels) in a cell, including symptoms of cancer of a subject is also provided. Such processes illustratively include administering to a subject a therapeutically effective amount of Type-A polymers.

Processes of treating symptoms implicated by dysfunctions the PD-1/PD-L1 pathway (such as dysregulated PD-L1 levels and particularly high PD-L1 levels, dysregulated PD-1 levels and particularly low PD-1 levels, or combinations thereof) in a subject, including symptoms of cancer, viral infections, and autoimmune diseases such as autoimmune dilated cardiomyopathy, lupus-like syndrome, autoimmune encephalomyelitis, systemic lupus erythematosus, graft-versus-host disease, and rheumatoid arthritis, illustratively include administering to a subject a composition including the active ingredient in a dosage so that each dose of the composition will deliver into the individual active ingredient in the amount of 0.1 milligrams (mg) to 150 mg of active ingredient per serving or any value or range therebetween, optionally 1-30 mg, optionally 3-10 mg.

It is further contemplated that variable dosing regiments are operative in the methods. While in some instances, a single dose treatment may be effective in producing therapeutic effects, in other instances a treatment period in the range of, for example, six weeks to three or six months or more may be utilized. The composition may be administered orally, parentally, or intravenously by intramuscular, intraperitoneal, by transdermal injection, or otherwise by contact with a subject. Injectables or oral forms may be prepared in conventional forms, either liquid solutions or suspensions, solid forms suitable for solution or prior to administration, or as suspension in liquid prior to administration or as emulsions.

The dose of the composition may vary depending on the age, weight, general condition of the subject. For example, dosage in the range of 1-1,000 mg of at least 0.5% active ingredient by dry weight per day may be an effective range. The active ingredient may also comprise 0.01%-100% of the dry weight of the composition. For example, an active ingredient composition may comprise 0.5%-50% of the dry weight of the composition.

Various embodiments of the present invention are illustrated by the following non-limiting examples. The examples are for illustrative purposes and are not a limitation on any practice of the present invention. It will be understood that variations and modifications can be made without departing from the spirit and scope of the invention.

EXAMPLES

In the present study, rat C6 glioma cells and human macrophage-like THP-1 cells were used to determine the effects of active agents.

Immunofluorescence studies were utilized to explore the effects of an active composition including doubly linked type-A polymers on PD-L1 proteins. Purified cinnamtannin B1 and cinnamtannin D1 are obtained from Planta Analytica (New Milford, Conn.). A water extract of cinnamon with at least 3% by weight doubly linked type-A polymers was obtained from IN Ingredients sold as CINNULIN PF. Each dried material was solvated in DMSO and stored at −20° C. until use. The antibodies (anti-PD-L1) were all obtained from Santa Cruz Biotech. All other reagents used were of the highest grade available in commercial products.

C6 glioma cells (CCL-107) were purchased from American Type Culture Collection (ATCC; Manassas, Va.). Cell cultures were grown in F-12 K medium (Gibco/Invitrogen) supplemented with 10% horse serum and 2% fetal bovine serum and maintained in a humidified atmosphere containing 5% $CO_2$ and 95% air at 37° C. Cultures were grown to 85% confluency in 75 mm flasks, and cells were subcultured by trypsinization of subconfluent cultures using 0.05% trypsin with EDTA. C6 glioma cells were seeded at a density of $0.5 \times 10^6$ cells per 35 mm dish, and cultured for two days. Cells were grown to confluence during the experimental period. Three studies were performed: 1) no other treatment of the cells; 2) treatment with LPS (10 μg/mL); and 3) treatment with TNF-α (10 ng/mL). In some studies, cells were incubated in fresh F-12K medium supplemented with either cinnamtannin D1 (at a concentration of 0 µg/ml, 5 µg/ml, 10 µg/ml, 20 µg/ml, 25 µg/ml, or 50 µg/ml) or cinnamtannin B1 (at a concentration of 0 µg/ml, 5 µg/ml, 10 µg/ml, 20 µg/ml, 25 µg/ml, or 50 µg/ml) for 24 h at 37° C. In certain treatment with LPS studies, the cells were incubated in fresh F-12 K medium supplemented with 10 µg/mL LPS or incubated in fresh F-12 K medium supplemented with 10 µg/mL LPS and cinnamtannin D1 at a concentration 10 µg/ml or 50 µg/ml (5 µg/ml and 25 µg/ml were not tested) for 24 h at 37° C. In certain treatment with TNF-α studies, the cells were incubated in fresh FK-12 medium supplemented with 10 ng/mL TNF-α and cinnamtannin D1 at a concentration 10 µg/ml, 20 µg/ml or 50 µg/ml (5 µg/ml was not tested) for 24 h at 37° C.

Human monocytic THP-1 cells were purchased from ATCC, Manassas, Va. and were maintained in RPMI culture medium supplemented with 10% heat inactivated fetal bovine serum and 50 pM β-mercaptoethanol in a humidified atmosphere containing 5% $CO_2$ and 95% air at 37° C. THP-1 monocytes are differentiated in macrophages by 24 hour incubation with 150 nM phorbol 12-myristate 13-acetate (PMA, Sigma, P8139). Two studies were performed: 1) no other treatment of the cells; and 2) treatment with LPS (10 µg/mL). For the no other treatment studies, the cells were incubated in fresh RPMI medium supplemented with the noted concentrations of extract of 0 µg/ml, 5 µg/ml, 10 µg/ml, or 25 µg/ml for 72 h at 37° C. For the treatment with LPS studies, the cells were incubated in fresh RPMI medium supplemented with 10 µg/mL of LPS and a concentration of active of 0 µg/ml, 5 µg/ml, 10 µg/ml, 20 µg/ml, or 50 µg/ml for 24 h at 37° C.

Cells were rinsed with ice-cold PBS and fixed with 4% paraformaldehyde for 10 min at room temperature, followed by permeabilization with 0.3% Triton x-100 for 10 min. After being washed with PBS three times, cells were incubated for 1 h in PBS containing 10% normal goat serum blocking solution. The cells were subjected to immunofluorescence staining with the specific antibodies (Rat C6 glioma cells studied for PD-L1 (Santa Cruz Biotech). The cells were then washed with cold PBS three times for 3 min each, and incubated with Alexa-labeled secondary antibodies (Invitrogen) at room temperature for 1 h. The cells were examined by fluorescence microscopy (a Nikon TE2000-S microscope, Nikon, Tokyo, Japan). For cell counts, five to ten random fields with approximately similar density of cells in each field were selected for analysis in each plate. Fluorescence intensities (with pixel values exceeding five times the standard deviation of the background) from these images were semi-quantitatively analyzed by densitometry (ImageJ software, NIH Image).

As depicted in FIG. 1, the cinnamtannin D1 significantly inhibited PD-L1 expression in rat C6 glioma cells at all concentrations tested. As compared to controls, cinnamtannin D1 resulted in a percent inhibition of PD-L1 expression of 39.9 percent inhibition at 5 µg/ml of cinnamtannin D1, 66.8 percent inhibition at 10 µg/ml of cinnamtannin D1, 58.1 percent inhibition at 25 µg/ml of cinnamtannin D1, and 43.6 percent inhibition at 50 µg/ml of cinnamtannin D1.

Figure 2:
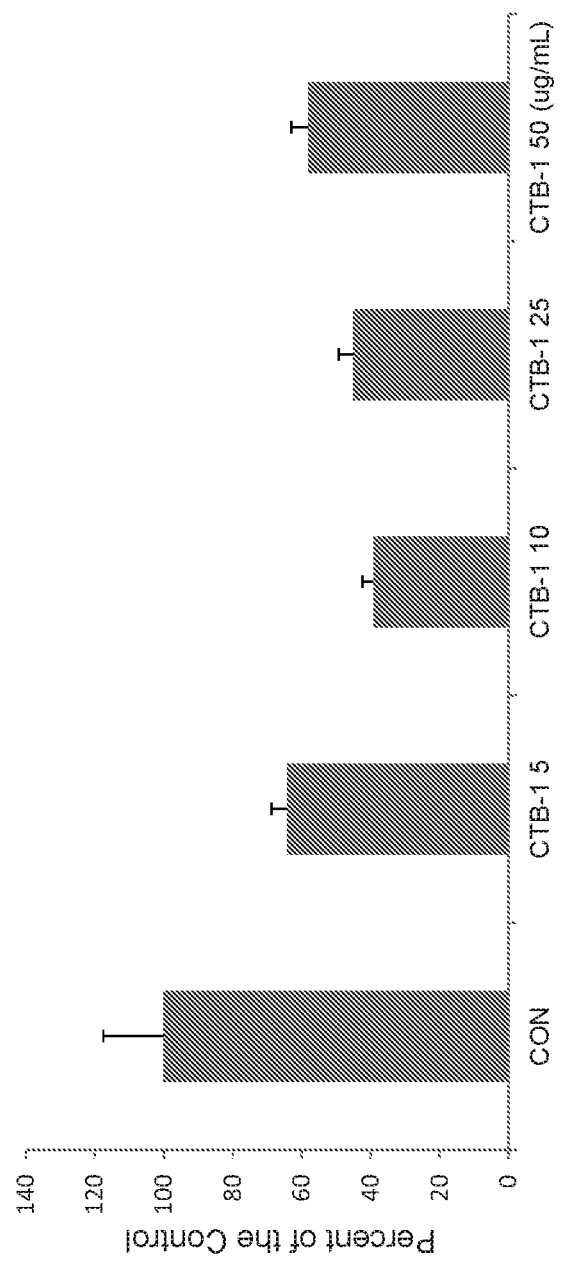
FIG. 2 graphically depicts the effects on PD-L1 expression as quantitative densitometry results of immunofluorescence studies for rat C6 glioma cells treated with cinnamtannin B1 at a concentration of at 0 µg/ml, 5 µg/ml, 10 µg/ml, 25 µg/ml, or 50 µg/ml for 24 hours at 37° C. where results are expressed as the mean±SD of five to ten random fields with approximately similar density of cells in each field in each plate.

As depicted in FIG. 2, the cinnamtannin B1 significantly inhibited PD-L1 expression in rat C6 glioma cells at all concentrations tested. As compared to controls, cinnamtannin B1 resulted in a percent inhibition of PD-L1 expression of 35.7 percent inhibition at 5 µg/ml of cinnamtannin B 1, 60.8 percent inhibition at 10 µg/ml cinnamtannin B1, 54.9 percent inhibition at 25 µg/ml of cinnamtannin B1, and 41.9 percent inhibition at 50 µg/ml of cinnamtannin B1.

Figure 3:
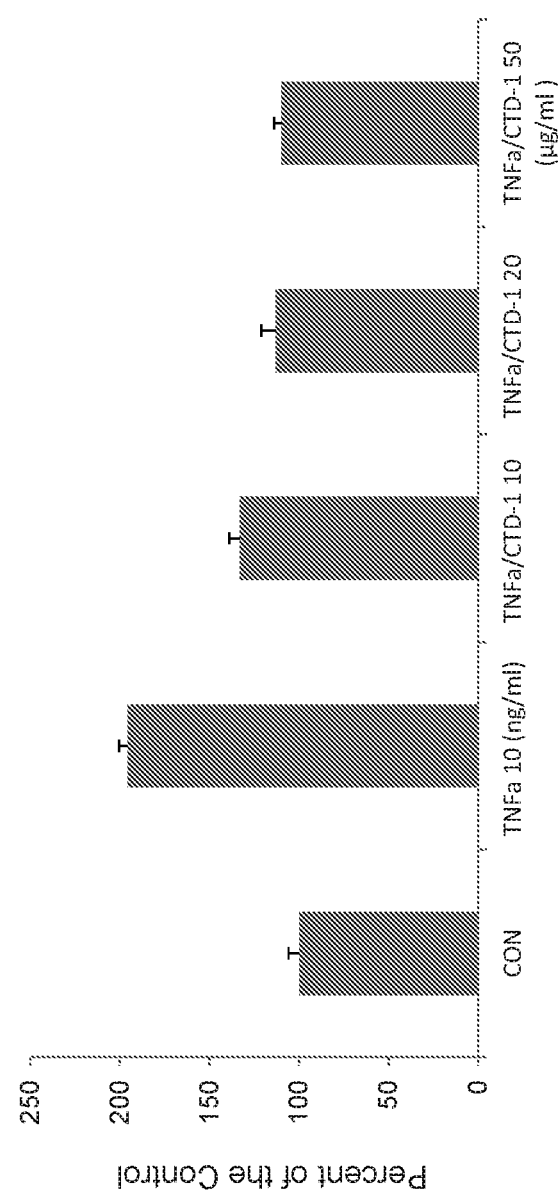
FIG. 3 graphically depicts the effects on TNF-α-induced overexpression of PD-L1 as quantitative densitometry results of immunofluorescence studies for rat C6 glioma cells treated with TNF-α at 10 ng/ml and cinnamtannin D1 at a concentration of at 0 µg/ml, 10 µg/ml, 20 µg/ml, or 50 µg/ml for 24 hours at 37° C. where results are expressed as the mean±SD of five to ten random fields with approximately similar density of cells in each field in each plate.

As depicted in FIG. 3, the cinnamtannin D1 significantly inhibited TNF-α-induced overexpression of PD-L1 at all concentrations tested. As compared to controls, cinnamtannin D1 resulted in a percent inhibition of TNF-α-induced overexpression of PD-L1 of 32.0 percent inhibition at 10 µg/ml of cinnamtannin D1, 42.2 percent inhibition at 20 µg/ml of cinnamtannin D1, and 43.9 percent inhibition at 50 µg/ml of cinnamtannin D1.

Figure 4:
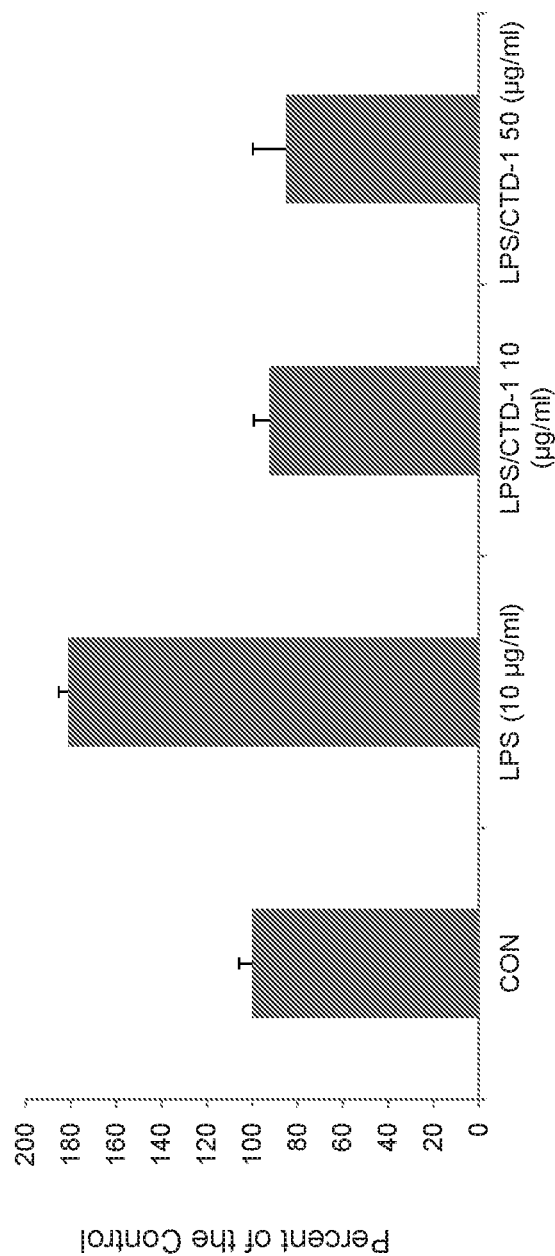
FIG. 4 graphically depicts the effects on LPS-induced overexpression of PD-L1 as quantitative densitometry results of immunofluorescence studies for rat C6 glioma cells treated with LPS at 10 µg/ml and cinnamtannin D1 at a concentration of at 0 µg/ml, 10 µg/ml, or 50 µg/ml for 24 hours at 37° C. where results are expressed as the mean±SD of five to ten random fields with approximately similar density of cells in each field in each plate.

As depicted in FIG. 4, the cinnamtannin D1 significantly inhibited LPS-induced overexpression of PD-L1 at all concentrations tested. As compared to controls, cinnamtannin D1 resulted in a percent inhibition of LPS-induced overexpression of PD-L1 of 48.9 percent inhibition at 10 µg/ml of cinnamtannin D1, and 53.0 percent inhibition at 50 µg/ml of cinnamtannin D1.

Figure 5:
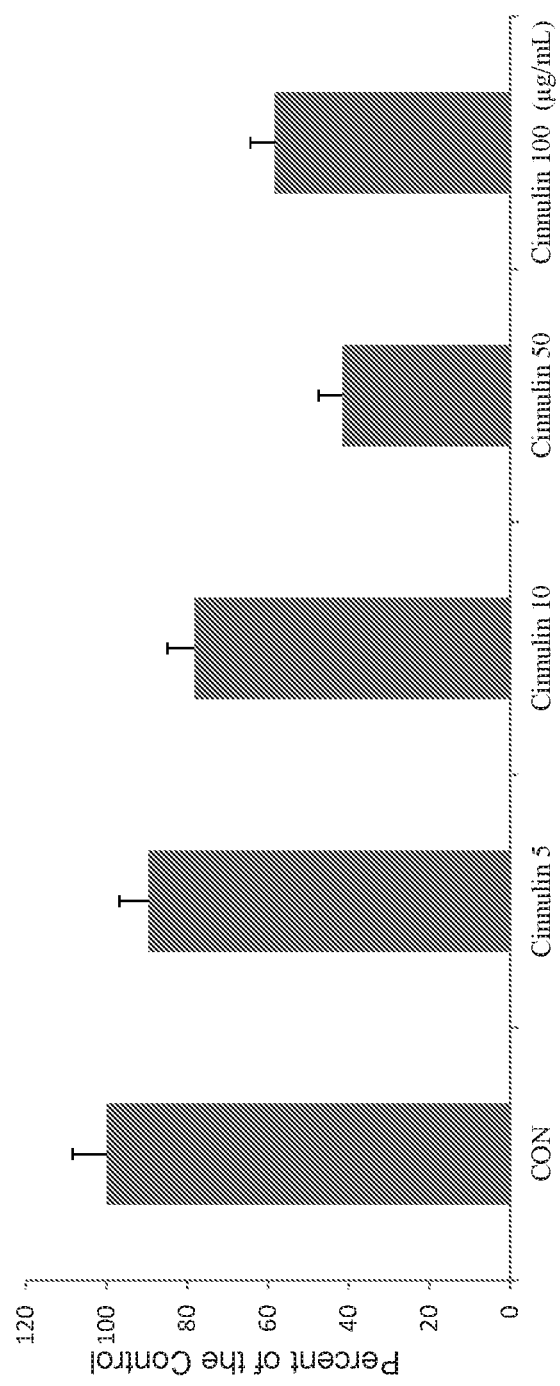
FIG. 5 graphically depicts the effects on PD-L1 expression as quantitative densitometry results of immunofluorescence studies for rat C6 glioma cells treated with a purified type-A polymer material with at least 3% by weight type-A polymers tested at a concentration of at 0 µg/ml, 5 µg/ml, 10 µg/ml, 50 µg/ml, or 100 µg/ml for 24 hours at 37° C. where results are expressed as the mean±SD of five to ten random fields with approximately similar density of cells in each field in each plate.

As illustrated in FIG. 5, the Type-A polymer composition (from 3% extract) produced significantly inhibited expression of PD-L1 relative to control in rat C6 glioma cells at all concentrations tested (5 µg/ml, 10 µg/ml, 50 µg/ml, or 100 µg/ml) showing inhibition of expression of 10.4%, 21.7%, 58.4%, and 41.7%, respectively. In additional data not shown, the Type-A polymer composition produced significantly inhibited LPS-induced overexpression of PD-L1 using both 10 µg/ml and 10 µg/ml concentrations (5 µg/ml and 20 µg/ml was not tested). Additionally, the Type-A polymer composition produced significantly inhibited TNF-α-induced overexpression of PD-L1 using 10 µg/ml, 20 µg/ml, and 50 µg/ml concentrations (5 µg/ml was not tested). Thus, the data demonstrates that doubly linked procyanidin type-A polymers significantly decrease expression of PD-L1 in cells.

It will be appreciated by persons skilled in the art that the present invention is not limited to what has been particularly shown and described herein above.

Various modifications of the present invention, in addition to those shown and described herein, will be apparent to those skilled in the art of the above description. Such modifications are also intended to fall within the scope of the appended claims.

It is appreciated that all reagents are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference for the entirety of their teaching.

The foregoing description is illustrative of particular aspects of the invention, but is not meant to be a limitation upon the practice thereof.

What is claimed is:

1. A process of decreasing expression of a CD274 gene or a PD-L1 protein in a glial tumor cell in a subject comprising:
   administering to the subject 1-3 times daily for a period of 6 weeks or more a composition comprising cinnamtannin D1 and/or cinnamtannin B1, the glial tumor cell expressing a CD274 gene or a PD-L1 protein; wherein the cinnamtannin D1 and/or cinnamtannin B1 are at a concentration within said composition sufficient to decrease expression of the CD274 gene or the PD-L1 protein in said glial tumor cell; whereby said administration decreases the expression of the CD274 gene or the PD-L1 protein in said glial tumor cell.

2. The process of claim 1, wherein said composition comprises cinnamtannin B1 at a concentration of greater than or equal to 10 weight percent.

3. The process of claim 1, wherein said composition comprises cinnamtannin D1 at a concentration of greater than 5 weight percent.

4. The process of claim 1, wherein said composition comprises 5 weight percent or greater cinnamtannin D1 and cinnamtannin B1.

5. The process of claim 1, wherein said cinnamtannin D1 and/or cinnamtannin B1 is present at about 1-30 milligrams.

6. The process of claim 1, wherein said cinnamtannin D1 and/or cinnamtannin B1 is present at about 3-10 milligrams.

7. A process of decreasing expression of a CD274 gene or a PD-L1 protein in a glial tumor cell expressing a CD274 gene or a PD-L1 protein in a subject comprising:
   administering to the subject a composition comprising cinnamtannin D1 and/or cinnamtannin B1;
   wherein the cinnamtannin D1 and/or cinnamtannin B1 are at a concentration within said composition sufficient to decrease expression of the CD274 gene or the PD-L1 protein in said glial tumor cell by said step of administering.

8. The process of claim 7 wherein said step of administering is 1-3 times per day.

9. The process of claim 7 wherein the step of administering is for a period of 6 weeks or more.

10. The process of claim 7, wherein said composition comprises cinnamtannin B1 at a concentration of greater than or equal to 10 weight percent.

11. The process of claim 7, wherein said composition comprises cinnamtannin D1 at a concentration of greater than 5 weight percent.

12. The process of claim 7, wherein said composition comprises 5 weight percent or greater cinnamtannin D1 and cinnamtannin B1.

13. The process of claim 7, wherein said cinnamtannin D1 and/or cinnamtannin B1 is present at about 1-30 milligrams.

14. The process of claim 7, wherein said cinnamtannin D1 and/or cinnamtannin B1 is present at about 3-10 milligrams.

15. A process of treating a subject having a tumor that expresses a CD274 gene or a PD-L1 protein in a tumor expressing a CD274 gene or a PD-L1 protein comprising:
   administering to the subject a composition comprising cinnamtannin D1 and/or cinnamtannin B1;
   wherein the cinnamtannin D1 and/or cinnamtannin B1 are at a concentration within said composition sufficient to decrease expression of the CD274 gene or the PD-L1 protein in said tumor by said step of administering.

16. The process of claim 15 wherein the step of administering is 1-3 times daily for a period of 6 weeks or more.

* * * * *